United States Patent [19]

Knifton

[11] 4,013,584
[45] Mar. 22, 1977

[54] PROCESSES FOR REGENERATING DISPERSIONS OF LIGAND-STABILIZED, PALLADIUM AND PLATINUM (II) HALIDE COMPLEXES USED IN CARBONYLATION AND HYDROFORMYLATION CATALYSIS

[75] Inventor: John F. Knifton, Poughquag, N.Y.

[73] Assignee: Texaco Inc., New York, N.Y.

[22] Filed: May 27, 1975

[21] Appl. No.: 581,320

[52] U.S. Cl. .......................... 252/415; 252/429 R; 260/410.9 R; 260/429 R; 260/429.7; 260/468 M; 260/497 R; 260/514 M; 260/515 R; 260/533 A; 260/604 HF; 260/666 R; 260/676 R

[51] Int. Cl.² .................... B01J 31/40; B01J 27/32; C07C 51/00; C11C 3/02

[58] Field of Search ............... 252/415, 414, 429 R; 260/410.9 R, 414, 533 A

[56] References Cited

UNITED STATES PATENTS

| 3,420,873 | 1/1969 | Olivier | 252/415 |
| 3,455,989 | 7/1969 | Kutepow et al. | 260/514 M |
| 3,641,076 | 2/1972 | Booth | 260/429 R |
| 3,700,706 | 10/1972 | Butter | 260/410.9 R |
| 3,832,391 | 8/1974 | Parshall | 260/413 |

*Primary Examiner*—Patrick P. Garvin
*Assistant Examiner*—P. E. Konopka
*Attorney, Agent, or Firm*—T. H. Whaley; C. G. Ries; Bernard Marlowe

[57] ABSTRACT

This invention concerns chlorinating processes for the regeneration of carbonylation and hydroformylation catalysts consisting of dispersions of ligand-stabilized palladium(II) and platinum(II) halide complexes in quaternary ammonium, phosphonium and arsonium salts of trihalostannate(II) and trihalogermanate(II).

5 Claims, No Drawings

PROCESSES FOR REGENERATING DISPERSIONS OF LIGAND-STABILIZED, PALLADIUM AND PLATINUM (II) HALIDE COMPLEXES USED IN CARBONYLATION AND HYDROFORMYLATION CATALYSIS

STATEMENT OF THE INVENTION

This invention pertains to the art of regenerating spent noble metal catalyst complexes useful for the carbonylation, hydroformylation and hydrogenation of olefins.

More particularly, this invention concerns the regeneration of certain carbonylation and hydroformylation catalysts consisting of dispersions of ligand-stabilized palladium(II) and platinum(II) halide complexes in quaternary ammonium, phosphonium and arsonium salts of trihalostannate(II) and trihalogermanate(II).

A. BACKGROUND OF THE INVENTION

This invention concerns a process for regenerating certain noble metal catalysts used in the carbonylation, hydroformylation and hydrogenation of olefins. Carbonylation refers here to the reaction of an olefin with carbon monoxide and an active-hydrogen-containing compound selected from the group consisting of an alkanol or water. This reaction is exemplified in eq. 1, wherein $R_1$, $R_2$, $R_3$ and $R_4$, individually, are hydrogen, alkyl up to 12 carbon atoms, alkenyl or up to 12 carbon atoms, or aryl up to 12 carbon atoms, or mixed alkyaryl or arylalkyl groups.

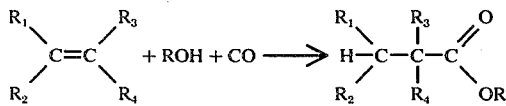

Suitable alkanols (ROH) include primary and secondary alcohols of 1 to 12 carbons, phenols, substituted alcohols and polyols. The major products of carbonylation are fatty (carboxylic) acids and their esters.

Hydroformylation is conducted by the reaction of a mixture of olefin, carbon monoxide and hydrogen, in the presence of a suitable catalyst. The process of hydroformylation may be expressed by eq. 2, wherein $R_1$, $R_2 R_3$ and $R_4$ are defined as above. The major products are aldehydes or alcohols.

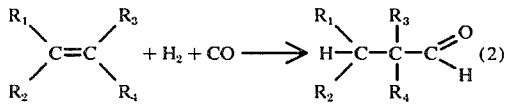

The preparation of the fatty acids or fatty esters using metal carbonyls or carbonyl precursons to catalyze the carbonylation of olefins (eq. 1) is old in the literature, originally involving Reppe and his coworkers and contemporaries. Reviews by C. W. Bird [Chem Rev. 62, 283 (1962)] document this work. Unfortunately, many of these carbonyl-type catalysts have the disadvantages of inherent toxicity, they require stringent reaction conditions which in turn lead to competing side reactions such as olefin isomerization, polymerization and reduction, and they exhibit poor selectivity to the desired linear acid ester.

Recently, more acceptable homogeneous catalyst systems have been developed which offer substantially improved selectivity in converting olefins to primarily linear fatty acids or linear fatty esters, in good yield, under moderate reaction conditions of temperature and pressure.

As is usually the case, after much more extensive usage, certain drawbacks have become more evident. These include difficulty in maintaining high conversions, high selectivities and high yields after recycling the catalyst several times. These problems are due to catalyst degradation as well as catalyst decomposition, mechanical losses and further catalyst decomposition during the separation of the products from the homogeneous catalysts and the inert solvents of the reaction mixture. Thermal instability of the catalyst is particularly troublesome in the recovery and working-up of certain ligand-stabilized homogeneous palladium catalyst reaction mixtures.

In order to avoid or minimize these problems, the use of molten quaternary ammonium, phosphonium and arsonium salts of trihalostannate(II) and trihalogermanate(II) as both solvent and part of the catalyst entity has been disclosed, particularly in the two U.S. Pat. Nos. of G. W. Parshall, 3,657,368 and 3,565,823 which are believed to be the closest known art except for applicant's more recently filed Ser. No. 526,867 filed 11/25/74 in the United States Patent Office.

However, in order to develop a commercially acceptable regeneration catalytic process it is necessary to demonstrate several key positive advantages:

1. A simple and efficient means of separating catalyst from the products,
2. The ability to recycle the catalyst without its substantial deactivation. This is particularly important in the case of the thermally sensitive palladium catalysts.
3. Regeneration processes which are capable of restoring the activity of the deactivated catalyst, particularly at high concentrations of catalysts up to 0.1 mole % concentration in the feed.

In this application are disclosed two different illustrative procedures for isolating organic products such as are produced by olefin carbonylation, hydroformylation and hydrogenation. These organic products may be separated in high purity from the palladium and platinum catalysts consisting of dispersions of ligand-stabilized palladium(II) halide and platinum(II) halides in quaternary ammonium, phosphonium and arsonium salts of trihalostannate(II) and trihalogermanate(II) by the procedures disclosed infra, and the palladium or platinum catalysts recycled with fresh olefin feed. The most important aspect of this application is the claimed process for restoring the activity of the above mentioned spent catalyst dispersion of the palladium(II) or platinum salts in quaternary ammonium, phosphonium and arsonium salts of trihalostannate(II) and trihalogermanate(II) by the treatment described below.

B. RECYCLING PROCESSES FOR PALLADIUM CARBONYLATION CATALYSTS, SUCH AS ARE DISCLOSED IN SERIAL NO. 526,867

While the claims of the inventive regeneration process are primarily directed to the regeneration of spent catalysts obtained by carbonylation, hydroformylation or hydrogenation process utilizing dispersions of platinum(II) or palladium(II) halides dispersed in quaternary ammonium, phosphonium or arsonium salts of trihalostannate(II) and trihalogermanate(II), in fact the inventive process can be employed to regenerate spent catalysts from unrelated processes. After the termination of the preparative process, many other isolation procedures can be used. Two isolation processes have been illustrated. In the first case, the product typified by an ester, is isolated by solvent extraction with a solvent such as petroleum ether. This extraction procedure (Procedure I) is as described below.

a. Separate the crude product liquid from the solid catalyst by filtration or decantation.

b. Distill the liquid product under atmospheric pressure or less (1 cm to 75 cm Hg.) to strip off unreacted olefin and alkanol.

c. Treat the liquid residue from step b) with a suitable organic solvent, such as petroleum ether, so as to extract the product fatty acid ester fraction into the solvent phase, and precipitate any dissolved catalyst melt.

d. Fractionally distill the organic solvent extract from step (c) under reduced pressure (1 mm to 75 cm Hg.) to recover fatty acid ester products.

e. Combine the recovered solid catalyst from steps (a) and (c), and recycle with additional olefin and alkanol, and CO under pressure.

The solvents employed in the inventive process of Procedure I, part c, to isolate the catalyst from the ester products are not critical as to volume or type. For convenience sake about 0.1 parts by volume to $10^3$ parts by volume of organic solvent is employed for each part by volume of catalyst. Suitable organic solvents include among others: paraffinic solvents such as petroleum ethers, heptane, hexane and n-octane etc., chlorinated solvents such as o-dichlorobenzene, chloronaphthalene etc., nitrocompounds including nitrobenzene, o-nitroanisole, p-nitroanisole nitromethane and 2-nitropropane, ketones such as methyl isobutyl ketone, acetone and methyl ethyl ketone, sulphones such as dimethylsulfone as well as dimethylsulfoxides, ethers such as diethyl ether, aromatics such as benzene, toluene and xylenes, acetonitrile and related compounds, and mixtures thereof.

This procedure for product ester recovery is illustrated in Example 1, described infra.

A second, alternative, method of separating the organic products, such as esters, from the solid catalyst involves a distillation procedure, as follows.

a. Separate the crude product from the solid catalyst by filtration or decantation.

b. Distill the liquid product under atmospheric pressure or less (1 cm to 75 cm Hg.) to recover unreacted olefin and alkanol.

c. Fractionally distill the residual liquid from step (b) under reduced pressure (1 mm to 75 cm Hg.) to recover fatty acid ester product.

d. Combine the recovered solid catalyst from steps (a) and (c), add additional olefin and alkanol, and recycle the reaction mix with CO under pressure.

This procedure for product ester recovery is illustrated in Examples 2 and 3, described infra.

EXAMPLE 1

PREPARATION OF METHYL NONANOATE WITH RECOVERY BY SOLVENT EXTRACTION

To a degassed sample of 1-octene (400 mmole) and methanol (30 ml.) contained in a 300 cc reactor equipped for pressurizing, heating, cooling and means of agitation is added under a nitrogen environment, tetraethylammonium trichlorostannate(II) (42 mmole) and bis(triphenylphosphine) palladium(II) chloride (4.4 mmole). The reactor is sealed, deoxygenated with a purge of nitrogen, and pressurized under carbon monoxide (1500 psig) while heating the agitated mixture between 80° and 90° C for 3-10 hours. At the end of this time the reaction is terminated by cooling and venting the reactor. The crude liquid product (79 ml.) is filtered to remove solid palladium catalyst, rotary evaporated at 40°-60° C under 2-20 cm Hg. pressure, and extracted with 200 ml. of petroleum ether in three portions. The combined ether extracts are distilled at 40° C (2-60 cm Hg.), and the methyl nonanoates recovered as residual liquid (60 ml. purity 95%).

The recovered 18.1 g of palladium catalyst from the above experiment is charged to a second degassed sample of 1-octene (400 mmole) and methanol (30 ml.), and the mixture carbonylated as described supra. The methyl nonanoate ester is recovered by solvent extraction as above, the solid palladium catalyst is then recycled with two additional batches of fresh 1-octene, methanol mixture. A summary of the octene conversion, and methyl nonanoate selectivity and yield data for the four catalyst cycles is given in Table 1. Gas chromatographic analyses were used to determine the conversion and selectivity data.

TABLE 1

PALLADIUM CARBONYLATION CATALYST RECYCLE STUDIES - METHYL NONANOATE SYNTHESIS
MELT COMPOSITION: $[(C_2H_5)_4N][SnCl_3]$-$PdCl_2[P(C_6H_5)_3]_2$

| | Cycle | Octene Conv (%) | Methyl Nonanoates[c] Selectivity (%)[d] | Yield (Mole %)[e] | Isolated Ester Purity (%) | Total Liquid Yield (%) |
|---|---|---|---|---|---|---|
| EXAMPLE 1: | | | | | | |
| | I[a] | 80 | 86.3 | 85 | 95 | 85 |
| | II | 80 | 86.5 | 81 | 95 | 88 |
| | III | 74 | 89.5 | 72 | 96 | 94 |
| | IV | 29 | 90.6 | 25 | 98 | 96 |
| EXAMPLE 2: | | | | | | |
| | I[b] | 80 | 83.1 | 82 | 99 | 90 |
| | II | 61 | 89.3 | 61 | 99 | 91 |
| | III | N.D. | 89.0 | 60 | 99 | 90 |
| | IV | 32 | 87.8 | 28 | 99 | 87 |

[a]Run Conditions: 85° C, 1500 psig. CO, 10 hr., [Sn]/[Pd]=9.6, initial [1-octene]/[Pd]=92, [CH$_3$OH]/[1-octene]=1.9
[b]Run Conditions: 85° C, 1500 psig. CO, 8 hr., [Sn]/[Pd]=10, initial [1-octene]/[Pd]=100, [CH$_3$OH]/[1-octene]=1.9
[c]A mixture of methyl nonanoate with some methyl 2-methyl octanoate and methyl 2-ethylheptanoate.
[d]Selectivity to linear methyl nonanoate based on total methyl nonanoate/total methyl C$_9$ ester.
[e]Yield based on octene charged.

EXAMPLE 2

PREPARATION OF METHYL NONANOATE WITH RECOVERY BY DISTILLATION

To a degassed sample of 1-octene (400 mmole) and methanol (30 ml.) contained in a reactor equipped for pressurizing, heating, cooling, and means of agitation is added under a nitrogen environment, tetraethylammonium trichlorostannate(II) (40 mmole) and bis(triphenylphosphine)palladium(II) chloride (4.0 mmole). The reactor is sealed, deoxygenated with a purge of nitrogen, and pressured under carbon monoxide (1500 psig) while heating the agitated mixture between 80° and 90° C for 3–8 hours. At the end of this time, the reaction is terminated by cooling and venting the reactor. The crude liquid product (83 ml.) is recovered by decantation, rotary evaporated at 40°–60° C under standard deviation after the 5th cycle is only 7.8%. Variations in linear fatty acid ester selectivity within each cycle are never greater than ∓3%, and are below 1% on the 5th cycle.

d. Storage stability of the catalysts is also good. A sample of recovered catalyst from the second cycle shows good activity even after storage in air for 10 days.

e. The purity of the isolated ethyl nonanoates (determined by glpc) remains essentially constant over 5 cycles at >99%.

TABLE 2

PALLADIUM CATALYST REPRODUCIBILITY STUDIES - ETHYL NONANOATE SYNTHESIS[a]
CATALYST COMPOSITION: $[(C_2H_5)_4N][SnCl_3]\text{-}PdCl_2[P(C_6H_5)_3]_2$

| CATALYST: | Cycle 1 | | Cycle 2 | | Cycle 3 | | Cycle 4 | | Cycle 5 | |
|---|---|---|---|---|---|---|---|---|---|---|
| | Sample 1 | Sample 2 | Sample 1 | Sample 2 | Sample 1 | Sample 2 | Sample 1 | Sample 2 | Sample 1 | Sample 2 |
| Ethyl $C_9$ Ester | | | | | | | | | | |
| Linearity (%) | 69.9 | 68.1 | 78.3 | 84.3 | 87.7 | 89.8 | 89.5 | 91.4 | 91.4 | 90.9 |
| Yield by G.C. (Mole %) | 84 | 88 | 86 | 85 | 81 | 62 | 79 | 45 | 15 | 26 |
| Yield Isolated (Mole %) | 79 | 78 | 77 | 76 | 71 | 51 | 67 | 31 | 11 | 19 |
| Purity (%) | >99 | >99 | >99 | >99 | >99 | >99 | >99 | >99 | >99 | >99 |
| Liquid Yield (%) | 93 | 90 | 97 | 99 | 100 | 99 | 100 | 100 | 100 | 100 |

[a]Run at 85°, 1500 psig. CO, 8 hr., [Sb]/[Pd]=10, [1-octene]/[Pd]=63, [$C_2H_5OH$]/[1-octene]=1.0

2–10 cm Hg. pressure, and the residual liquid fractionally distilled at 1–3 mm Hg. pressure. The fraction distilled at 1–3 mm Hg. pressure. The fraction distilling at 48°–51° C is identified by nmr, ir, glpc and elemental analyses as methyl nonanoates (60 ml., purity >99%).

The recovered solid palladium catalyst from the above experiment is charged to a second degassed sample of 1-ocetene (400 mmole) and methanol (30 ml.), and the mixture carbonylated as described supra. On cooling, the methyl nonanoate ester is recovered by the distillation procedure described, and the palladium catalyst is then recycled with two further batches of fresh 1-octene, methanol mixture. A summary of the octene conversion, and methyl nonanoate selectivity and yield data for the four catalyst cycles is given in Table 1.

EXAMPLE 3

PREPARATION OF ETHYL NONANOATE WITH RECOVERY BY DISTILLATION

Using the same general procedure as described in Example 2, additional runs are made with 1-octene, ethanol mixture and two samples of the catalyst system:

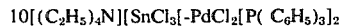

$10[(C_2H_5)_4N][SnCl_3[\text{-}PdCl_2[P(C_6H_5)_3]_2$

A total of ten batches of 1-octene, ethanol mixture were carbonylated by the procedure of Example 2, five batches for each catalyst sample. The purpose was to determine the degree of reproducibility of the palladium catalyst for ethyl nonanoate synthesis. The data are summarized in Table 2, some conclusions are as follows:

a. While olefin conversions and nonanoate ester yields remain essentially the same over the first three cycles, catalyst deactivation evidently starts to have a substantial deterrent on product yield in subsequent cycles.

b. Selectivity to be linear nonanoate ester improves steadily with successive recycling.

c. Samples of the palladium catalyst show good reproducibility. The yield data in Table 2 for the two catalyst samples agree within ∓2% for cycle 1, and the

C. REGENERATION OF PALLADIUM CARBONYLATION CATALYSTS

The regeneration of deactivated dispersions of ligand-stabilized palladium(II) halide in quaternary ammonium, phosphonium and arsonium salts of trihalostannate(II) or trihalogermanage(II) may be carried out by various techniques. Two useful methods that have been successfully applied to fatty acid ester synthesis are described in the following examples. The procedure for regenerating dispersions of palladium catalyst via treatment with chlorine gas alone (in the absence of an inert solvent during the chlorination step) is exemplified in Example 4. Here the 1-octene, ethanol mixture is carbonylated by the procedure of Example 2, and the ethyl nonanoate ester is recovered by distillation. After 3–6 cycles, the solid catalyst is regenerated as follows:

a. Chlorine is passed over the spend solid catalyst as 25°–200° C for 1–48 hours.

b. Additional stabilizing ligand, such as triphenylphosphine, is added to the cooled melt after chlorine treatment in the mole ratio 1–10 mole ligand per mole Pd.

c. The regenerated catalyst is refluxed with excess organic solvent mixture, the excess liquid removed, and the solid catalyst dried in vacuo.

Generally speaking, the amount of chlorine employed is not critical to the success of regeneration. A convenient mode of supplying sufficient chlorine is to hook-up a flow meter into the regeneration system and to permit the chlorine to contact the spent catalyst for a period of 1 to 48 hours preferably between 4 to 12 hours at a rate of between 1 and 500 cc per minute. Regeneration is considered to have occurred when a sample of chlorine treated catalyst delivers a selectivity of between 70 and 95% methyl nonanoate and a yield of from 20 to 95 mole %, reaction conditions being those set forth in Tables 2 and 4, the reagents and concentrations being those disclosed in the Tables 2 and 4 footnotes.

The organic solvent refluxed with the regenerated catalyst in step (c), after $Cl_2$ treatment, is preferably an equivolume mixture of olefin plus alkanol, the olefin and alkanol being preferably those selected for subsequent carbonylation steps. For example, in a series of syntheses of ethyl nonanoate, the regenerated catalyst is refluxed with a mixture of 1-octene plus ethanol. Other organic solvents may also be used to reflux the $Cl_2$-treated catalyst in step (c) however, including paraffinic solvents such as petroleum ethers, heptane, hexane etc., chlorinated solvents such as o-dichlorobenzene, chloronaphthalene, carbon tetrachloride, chloroform and dichloromethane, etc., nitrocompounds including nitrobenzene, o-nitroanisole, nitrotoluene, nitromesitylene, nitromethane and 2-nitropropane, ketones such as acetone, methyl isobutyl ketone, and methyl ethyl ketone, sulphones such as dimethylsulfone as well as dimethylsulfoxides, ethers such as diethyl ether, aromatics like benzene, toluene and xylenes, acetonitrile, and mixtures thereof.

Other palladium carbonylation catalysts beyond the $[(C_2H_5)_4N][SnCl_3]-PdCl_2]P(C_6H_5)_3]_2$ mixture descibed in Example 4 may also be regenerated by chlorine treatment. These palladium catalysts generally consist of ligandstabilized palladium(II) halide complexes dispersed in quaternary ammonium, phosphonium and arsonium salts of trihalostannate(II) and trihalogermanate(II). They are illustrated, but not limited by, the carbonylation catalysts described in Examples 5 to 11.

Other substrate mixtures beyond the 1-octene, ethanol used in Example 4, may also be carbonylated by the regenerated palladium carbonylation catalysts. Some typical examples are given in Examples 12-15, described infra.

Said dispersions of palladium catalyst may also be regenerated by treatment with chlorine in the presence of an inert organic solvent. This technique is illustrated in Example 16. Suitable inert solvents for the chlorination step may be selected from the group consisting of chlorinated aliphatics such as carbon tetrachloride, chloroform, dichloromethane, dichloroethane and chlorohexane, aromatic solvents such as benzene, toluene and xylenes, and chlorinated aromatics like o-dichlorobenzene, chlorobenzene and chlorotoluenes, and mixtures thereof.

EXAMPLE 4
PALLADIUM CATALYST REGENERATION VIA CHLORINE TREATMENT

This example uses the same carbonylation and product ester recovery techniques of Example 2, together with the same palladium catalyst dispersion, $10[(C_2H_5)_4N][SnCl_3]-PdCl_2[P(C_6H_5)_3]_2$, and 1-octene, ethanol liquid charge. Fresh tetraethylammonium trichlorostannate(II) (80 mmole) and bis (triphenylphosphine)palladium(II) chloride (8.0 mmole) are charged to a degassed mixture of 1-octene (0.5 mole) and ethanol (0.5 mole), and carbonylation is carried out in accordance with the procedure of Example 2. The ethyl nonanoate esters are recovered by distillation as also described in Example 2, and the recovered catalyst recycled with additional fresh feed (1-octene+ethanol). After the 5th, 9th, 13th and 16th cycle, the catalyst is regenerated by treatment with chlorine as follows:

a. The solid catalyst is transferred to a glass tube, and heated to 100°–150° C in a stream of chlorine (flow rate 10–200 cc/min) for 1 to 12 hours.

b. Triphenylphosphine (16 mmole) is added to the brown-colored catalyst.

c. The solid mix is refluxed with 100 ml. of 1:1 (V/V) ethanol, octene for 1hour under nitrogen, the excess liquid in the reaction mixture removed by distillation, and the solid catalyst dried in vacuo.

Table 3 summarizes the performance of the palladium catalyst over nineteen cycles. The total tabulated yield of ethyl nonanoates is 532 mole per gram atom of Pd, the maximum yield clearly exceeds this figure.

TABLE 3

PALLADIUM CATALYST REGENERATION VIA CHLORINE TREATMENT - ETHYL NONANOATE SYNTHESIS [a]

| Cycle | Octene Conv(%) | Linearity (%) | Ethyl $C_9$ Ester Yield(By G.C. Mole%) | Yield(Isolated,Mole%) | Purity(%) | Liquid Yield(%) |
|---|---|---|---|---|---|---|
| I | 97 | 66.2 | 77 | 80 | 99 | 92 |
| II | 87 | 77.1 | 82 | 75 | 99 | 93 |
| III | 43 | 91.2 | 56 | 56 | 99 | 102 |
| IV | 37 | 92.9 | 50 | 34 | 99 | 89 |
| V | 10 | 81.8 | 18 | 14 | 99 | 101 |
| VI | 80 | 85.5 | 71 | 60 | 99 | 90 |
| VII | 93 | 74.2 | 101 | 79 | 99 | 98 |
| VIII | 29 | 82.1 | 37 | 37 | 99 | 100 |
| IX | 2.7 | 81.6 | 3.1 | 6.9 | 99 | 100 |
| X | 82 | 82.7 | 80 | 42 | 99 | 70 |
| XI | 83 | 84.0 | 76 | 69 | 99 | 93 |
| XII | 20 | 84.6 | 18 | 14 | 99 | 100 |
| XIII | 7.2 | 87.7 | 1.0 | N.D. | N.D. | 100 |
| XIV | 71 | 82.2 | 87 | 66 | 99 | 100 |
| XV | 7.5 | 82.6 | 12 | 11 | 99 | 100 |
| XVI | 2 | 85.3 | 1.2 | 2.3 | 99 | 100 |
| XVII | 30 | 74.1 | 35 | 21 | 99 | 81 |
| XVIII | 42 | 80.4 | 48 | 29 | 99 | 100 |
| XIX | 8.2 | 79.8 | 4.9 | 3.7 | 99 | 93 |

[a]Run Conditions: Ξ°, 1500 psig. CO, 4–8 hr., [1-octene]/[Pd]=63, [Sn]/[Pd]=10, [ethanol]/[octene]=1.0

EXAMPLES 5-11 PALLADIUM CATALYST REGENERATION EFFECT OF CATALYST COMPOSITION

In these examples the carbonylation of 1-octene, ethanol samples are carried out in accordance with the procedure outlined in Example 4, but in the presence of various other ligand-stabilized palladium(II) halide complexes dispersed in quaternary ammonium, phosphonium and arsonium salts of trihalostannate(II) and trihalogermanate(II). The following catalyst compositions showed satisfactory performance for ethyl nonanoate synthesis over 8 cycles:

10[($C_2H_5$)$_4$N][$SnCl_3$]-$PdCl_2$[P(p-$CH_3$.$C_6H_4$)$_3$]$_2$
5[$ClCH_2$($C_6H_5$)$_3$P][$SnCl_3$]-$PdCl_2$[P($C_6H_5$)$_3$]$_2$
10[(n-$C_4H_9$)$_4$N[ ]$SnCl_3$]-$PdCl_2$[P($C_6H_5$)$_3$]$_2$
10[($C_6H_5$)$_4$As[ ]$SnCl_3$]-$PdCl_2$[P($C_6H_5$)$_3$]$_2$
5[($C_2H_5$)$_4$N][$GeCl_3$]-$PdCl_2$[P($C_6H_5$)$_3$]$_2$
10[($C_2H_5$)$_4$N][$SnCl_3$]-$PdCl_2$[P(p-$CH_3$O.$C_6H_4$)$_3$]$_2$
5[($C_7H_{15}$)$_4$N][$GeCl_3$]-$PdCl_2$[As($C_6H_5$)$_3$]$_2$

EXAMPLES 12–15

PALLADIUM CATALYST REGENERATION EFFECT OF CHANGES IN REACTANTS

In these examples, the carbonylation of samples of equimolar α-olefin-alkanol mixtures are carried out in accordance with the procedures outlined in Examples 1, 2 and 4 using the same dispersion of palladium complex in quaternary salt, viz.

10[($C_2H_5$)$_4$N][$SnCl_3$]-$PdCl_2$[P($C_6H_5$)$_3$]$_2$

The recovered solid palladium catalyst is charged to a second degassed sample of 1-octene (0.5 mole) and ethanol (0.5 mole), and the mixture carbonylated as described supra. On cooling, the ethyl nonanoate esters are recovered by the distillation procedure described, and the palladium catalyst is then recycled with two additional batches of fresh 1-octene, ethanol mixture.

After 4 cycles, the 35 gm of recovered solid palladium catalyst is regenerated as follows:

a. The solid catalyst is added to carbon tetrachloride (100 ml.) and heated to reflux for 1 to 12 hours in a stream of chlorine (flow rate 10–200 cc/min.).

b. Excess liquid is removed from the catalystcarbon tetrachloride mixture by distillation, and the solid residue dried in vacuo.

c. Triphenylphosphine (16 mmole) is added to the reddish-brown catalyst after drying.

Table 4 summarizes the performance of the palladium catalyst over twelve cycles, regeneration is repeated after the 9th cycle.

TABLE 4

| | PALLADIUM CATALYST REGENERATION VIA CHLORINE TREATMENT - ETHYL NONANOATE SYNTHESIS | | | | |
|---|---|---|---|---|---|
| Cycle | Octene Conv(%) | Linearity(%) | Ethyl $C_9$ Ester Yield(Mole%) | Purity(%) | Liquid Yield(%) |
| I | 88 | 69.6 | 84 | >99 | 88 |
| II | 90 | 88.9 | 87 | >99 | 95 |
| III | 22 | 91.0 | 21 | >99 | 99 |
| IV | <10 | 90.0 | 7.6 | >99 | 102 |
| V | 78 | 77.0 | 67 | >99 | 78 |
| VI | 76 | 80.0 | 81 | 99 | 80 |
| VII | 68 | 84.1 | 65 | >99 | 91 |
| VIII | <20 | 89.4 | 18 | >99 | 92 |
| IX | <5 | 92.7 | 2.0 | 99 | 92 |
| X | 24 | 82.5 | 25 | 73 | 96 |
| XI | 85 | 83.4 | 82 | 98 | 91 |
| XII | 79 | 81.8 | 77 | >99 | 93 |

The following olefin-alkanol mixtures gave good yields of the corresponding esters over 8 catalyst cycles:

| | |
|---|---|
| Propylene | 1-decanol |
| 1-hexene | iso-propanol |
| 1-decene | 2-chloroethanol |
| 1-tetradecene | methanol |

EXAMPLE 16

PALLADIUM CATALYST REGENERATION VIA CHLORINE TREATMENT

Using the general procedure of Example 2, a liquid mix of degassed 1-octene (0.5 mole) and ethanol (0.5 mole), together with the catalyst components tetraethylammonium trichlorostannate(II) (80 mmole) and bis(triphenylphosphine) (palladium(II) chloride (8.0 mmole), are charged to a 300 ml. glass-lines reactor, purged with $N_2$, and pressuring with CO (1500 psig) while heating to 80°–90° C for 3–8 hours. Carbonylation is terminated by cooling and venting the reactor. The crude product liquid (78–108 ml.) is recovered by decantation, rotary evaporated at 40°–60° under 2–10 cm Hg. pressure, and the residual liquid fractionally distilled at 1–3 mm Hg. pressure. The fraction distilling at 70°–75° C is identified as ethyl nonanoates (50–90 ml., purity >99%) by nmr, ir, glpc and elemental analyses.

D. REGENERATION OF PLATINUM HYDROFORMYLATION CATALYSTS

Bis(triphenylphosphine)platinum(II) chloride and related ligand-stabilized platinum(II) halide complexes, dispersed in quaternary ammonium, phosphonium and arsonium salts of trichlorostannate(II) and trihalogermanage(II) salts have been found to be excellent catalysts for the selective hydroformylation of olefins, particularly 1-olefins, to predominantly linear aldehyde derivatives. The product aldehyde may be recovered from the platinum catalyst by distillation or solvent extraction techniques, similar to those outlined in Examples 1 and 2 of this application. After multiple cycling, the platinum catalyst may be regenerated by treatment with gaseous chlorine. The general procedure is exemplified here for the synthesis of n-butyraldehyde from propylene.

EXAMPLE 17

PLATINUM CATALYST REGENERATION VIA CHLORINE TREATMENT

A sample of tetraethylammonium trichlorostannate(II) (40 mmole) and bis(triphenylphosphine)-platinum(II) chloride (4.0 mmole) are placed in a glasslined, 300 ml. autoclave reactor, the reactor sealed, purged with CO, and pressured to 1260 psig with 42 g of propylene (1 mole) plus a 1:1 (V/V) gas mixture of CO/$H_2$. The mixture is heated to 80° C, stirred for 5 hours at temperature, and allowed to cool. Forty grams of yellow liquid product are recovered by decantation from the yellow crystalline melt, and fractionally distilled. Butyraldehydes (34.5 g. 0.48 mole) are recovered from a fraction boiling 72°–75° C (1 atm), and identified by nmr, ir, glpc and elemental analyses.

The recovered solid platinum catalyst is returned to the reactor, the reactor purged with CO, and pressured to 1260 psig with a second 42 g batch of propylene (1mole) plus 1:1 (V/V) CO/H$_2$. Hydroformylation is carried out as described supra, and the butyraldehyde recovered by atmospheric distillation. After 3 cycles, the platinum catalyst is regenerated with chlorine as follows:

a. The solid catalyst is transferred to a glass tube, and heated to 100°–150° C in a stream of chlorine (flow rate 1–500 cc/min.) for 1 to 12 hours. b. Triphenylphosphine (8.0 mmole) is added to the reddish-brown colored catalyst.

c. The solid mix is refluxed with 100 ml. of solvent for an hour under nitrogen, the excess liquid recovered by distillation, and the solid catalyst dried in vacuo.

Table 5 summarizes the performance of the platinum melt over six cycles. It may be noted that the $[(C_2H_5)_4N][SnCl_3]$-P $_2[P(C_6H_5)_3]_2$ catalyst consistently gives n-butyraldehyde in 81–83 mole % selectivity, and the butyraldehydes isolated by this technique are at least 98% pure by glpc analysis.

Further, the invention processes are flexible in permitting changes and modifications to be made without departing from the inventive process.

However, the metes and bounds of this invention can best be gleaned by reading the claims that follow in conjunction with the rest of the specification.

What is claimed is:

1. A process for the regeneration of dispersions of spent ligand-stabilized palladium(II) or platinum(II) halide catalysts in quaternary ammonium, phosphonium and arsonium salts of trihalostannate(II) and trihalogermanate(II), the spent catalysts being obtained from the carbonylation or hydroformylation of olefins, said ligand-stabilized groups being selected from the group consisting of $P(C_6H_5)_3$, $P(p-CH_3.C_6H_4)_3$, $P(C_6H_5)_3CH_2Cl$, $As(C_6H_5)_3$, $S(C_6H_5)_2$, $P(OC_6H_5)_3$, $P(n-C_4H_9)_3$, $(C_6H_5)_2AsCH_2CH_2As(C_6H_5)_2$, the process consisting essentially of:

a. contacting the spent dispersions of catalyst with chlorine gas at 25° to 200° C for 1–48 hours at a flow rate between 1 and 500 cc per minute;

b. adding additional ligand corresponding to the original ligand contained in the dispersion of spent catalyst, prior to the catalyst's use in carbonylation, hydroformylation or hydrogenation reaction, the ligand being added at rates of 1–10 moles of ligand per mol of palladium or platinum present in the spent dispersion to be regenerated;

TABLE 5

PLATINUM CATALYST REGENERATION VIA CHLORINE TREATMENT - BUTRALDEHYDE SYNTHESIS[a]

| Cycle | -Butyraldehyde Selectivity(Mole%) | Yield of Butyraldehyde(Mole%) | | Purity of Isolated Butyraldehydes(%) |
|---|---|---|---|---|
| | | Calc. by glpc | Isolated | |
| I | 82 | 48 | 48 | 99 |
| II | 83 | 33 | 34 | 99 |
| III | 82 | 10 | 5.0 | 98 |
| IV | 81 | 45 | 44 | 99 |
| V | 82 | 30 | 28 | 99 |
| VI | 83 | 7 | 5.8 | 98 |

[a]Run Conditions: 80° C, 1260 psog of CO/H$_x$(1:1,V/V), 4–8 hr.; Initial (Propylene]/[Pt]=250,[Sn]/[Pt]-10.

EXAMPLES 18–24

PLATINUM CATALYST REGENERATION EFFECT OF CATALYST COMPOSITION

In these examples, the hydroformylation of propene to butyraldehydes is carried out in accordance with the procedure outline in Example 17, but in the presence of various other platinum(II) halide complexes dispersed in tetraethylammonium trichlorostannate(II). The following platinum salts showed satisfactory performance for butraldehydes synthesis over 6 cycles.

$PtCl_2[As(C_6H_5)_3]_2$
$PtCl_2[S(C_6H_5)_2]_2$
$PtCl_2[P(OC_6H_5)_3]_2$
$PtCl_2[P(n-C_4H_9)_3]_2$
$PtCl_2[(C_6H_5)_2AsCH_2As(C_6H_5)_2]$
$PtCl_2[O$-Phenanthroline$]$
$PtCl_2$ As the previous Tables and Discussions have indicated the catalyst regeneration procedures of this invention are both novel and useful. They may be applied to catalysts consisting of dispersions of palladium and platinum salts in quaternary ammonium, phosphonium and arsonium salts of trihalostannate(II) and trihalogermanate(II), useful in the catalytic carbonylation, hydroformylation and hydrogenation of olefins.

c. adding inert solvent to the chlorinated spent catalyst;

d. refluxing the catalyst-inert solvent mixture;

e. removing the excess inert solvent mixture, and f. drying the regenerated catalyst.

2. The process of claim 1 wherein the spend dispersions of palladium and platinum catalysts are treated with chlorine gas in the presence of an inert organic solvent.

3. The process of claim 2 wherein said inert solvent is selected from the group consisting of carbon tetrachloride, dichloromethane, dichlorethane and odichlorobenzene.

4. A process for regenerating dispersions of spent ligand-stablized palladium(II) and platinum(II) halide catalysts in quaternary ammonium, phosphonium and arsonium salts of trihalostannate(II) or trihalogermanate(II), said spent catalysts being obtained through carbonylation or hydroformylation of olefins, by the process consisting essentially of:

a. passing chlorine over spent catalysts selected from the group consisting of:

$[(C_2H_5)_4N][SnCl_3]$-$PdCl_2[P(C_6H_5)_3]_2$
$[(C_2H_5)_4N][SnCl_3]$-$PdCl_2[P(p-CH_3.C_6H_4)_3]_2$
$[ClCH_2(C_6H_5)_3P][SnCl_3]$-$PdCl_2[P(C_6H_5)_3]_2$
$[(n-C_4H_9)_4N][SnCl_3]$-$PdCl_2[P(C_6H_5)_3]_2$
$[(C_6H_5)_4As][SnCl_3]$-$PdCl_2[P(C_6H_5)_3]_2$ $[(C_2H_5)_4N][GeCl_3]\text{-}PdCl_2[P(C_6H_5)_3]_2$
$[(C_2H_5)_4N][SnCl_3]\text{-}PdCl_2[P(p\text{-}CH_3O.C_6H_4)_3]_2$
$](C_7H_{15})_4N][GeCl_3]\text{-}PdCl_2[As(C_6H_5)_3]_2$
$[(C_2H_5)_4N][SnCl_3]\text{-}PtCl_2[P(C_6H_5)_3]_2$
$[(C_2H_5)_4N][SnCl_3]\text{-}PtCl_2[As(C_6H_5)_3]_2$
$[(C_2H_5)_4N][SnCl_3]\text{-}PtCl_2[S(C_6H_5)_2]_2$
$[(C_2H_5)_4N][SnCl_3]\text{-}PtCl\ [\ ]P(OC_6H_5)_3]_2$
$[(C_2H_5)_4N][SnCl_3]\text{-}PtCl_2[P(n\text{-}C_4H_9)_3]_2$
$[(C_2H_5)_4N][SnCl_3]\text{-}PtCl_2[(C_6H_5)_2AsCH_2CH_2As(C_6H_5)_2]$
$[(C_2H_5)_4N][SnCl_3]\text{-}PtCl_2[O\text{-}Phenanthroline]$ and
$[(C_2H_5)_4N][SnCl_3]\text{-}PtCl_2[(C_6H_5)_3]_2$ at 25°–200° C for 1–48 hours at a flow rate between about 1 and 500 cc per minute;

b. adding additional stabilizing ligand in the ratio of 1–10 mole of ligand per mole of palladium or platinum present in said spent dispersions;

c. refluxing the mixture from b) in excess organic solvent mixture, removing excess solvent and drying the solid dispersion in a vacuum.

5. A process for regenerating dispersions of $[(C_2H_5)_4N][SnCl_3]\text{-}PdCl_2[P(C_6H_5)_3]_2$ catalyst spent in carbonylating olefins the process consisting essentially of:

a. passing chlorine over said spent catalyst at 25°–200° for 1–48 hours at a flow rate between about 1 and 500 cc per minute;

b. adding additional $P(C_6H_5)_3$ ligand in the ratio of 1–10 mole of ligand per mole of palladium present in said spent catalyst;

c. refluxing the mixture from (b) in excess alkanololefin solvent mixture, removing excess solvent and drying the solid dispersion in a vacuum.

* * * * *